US008523042B2

(12) United States Patent
Masiakos et al.

(10) Patent No.: US 8,523,042 B2
(45) Date of Patent: Sep. 3, 2013

(54) APPARATUS AND METHOD FOR PRESERVING A TISSUE MARGIN

(75) Inventors: Peter T Masiakos, Sudbury, MA (US); Andrew Rosenberg, Brookline, MA (US); Henning Gaissert, Dover, MA (US)

(73) Assignee: The General Hospital Corporation, Boston, MA (US)

( * ) Notice: Subject to any disclaimer, the term of this patent is extended or adjusted under 35 U.S.C. 154(b) by 328 days.

(21) Appl. No.: 12/909,298

(22) Filed: Oct. 21, 2010

(65) Prior Publication Data

US 2011/0089221 A1    Apr. 21, 2011

Related U.S. Application Data

(60) Provisional application No. 61/253,650, filed on Oct. 21, 2009.

(51) Int. Cl.
*A61B 17/068* (2006.01)

(52) U.S. Cl.
USPC .................. 227/180.1; 227/176.1; 227/19

(58) Field of Classification Search
USPC ..................................... 227/19, 176.1, 180.1
See application file for complete search history.

(56) References Cited

U.S. PATENT DOCUMENTS

| | | |
|---|---|---|
| 3,665,924 A | 5/1972 | Noiles et al. |
| 3,795,034 A | 3/1974 | Strekopytov et al. |
| 3,889,683 A | 6/1975 | Kapitanov et al. |
| 4,047,654 A | 9/1977 | Alvarado |
| 4,086,926 A | 5/1978 | Green et al. |
| 4,429,695 A | 2/1984 | Green |
| 4,665,916 A | 5/1987 | Green |
| 4,848,637 A * | 7/1989 | Pruitt ............................. 227/19 |
| 4,881,544 A | 11/1989 | Green et al. |
| 5,040,715 A | 8/1991 | Green et al. |
| 5,156,315 A | 10/1992 | Green et al. |
| 5,156,614 A | 10/1992 | Green et al. |
| 5,253,793 A | 10/1993 | Green et al. |
| 5,344,060 A | 9/1994 | Gravener et al. |
| 5,465,896 A | 11/1995 | Allen et al. |
| 5,651,491 A | 7/1997 | Heaton et al. |
| 5,662,260 A * | 9/1997 | Yoon .......................... 227/176.1 |
| 5,868,760 A | 2/1999 | McGuckin, Jr. |
| 6,109,500 A | 8/2000 | Alli et al. |
| 6,302,311 B1 | 10/2001 | Adams et al. |
| 6,343,731 B1 | 2/2002 | Adams et al. |
| 6,629,630 B2 | 10/2003 | Adams |
| 6,805,273 B2 | 10/2004 | Bilotti et al. |
| 7,004,950 B1 | 2/2006 | Collins et al. |
| 7,070,083 B2 * | 7/2006 | Jankowski ................. 227/176.1 |
| 7,235,089 B1 | 6/2007 | McGuckin, Jr. |

(Continued)

*Primary Examiner* — Brian D Nash
(74) *Attorney, Agent, or Firm* — Quarles & Brady, LLP

(57) ABSTRACT

A cartridge for a surgical apparatus includes a housing having a slot configured to accommodate a blade. A plurality of fasteners is configured to be deployed by the housing. A first row of the plurality of fasteners is positioned on a first side of the slot and a second row of the plurality of fasteners is positioned on a second side of the slot. The first row of the plurality of fasteners is the nearest row of fasteners to the slot on the first side of the slot that are deployed by the housing, and the first row of the plurality of fasteners is spaced apart from the slot such that an undamaged tissue margin is formed on a section of tissue during operation of the surgical apparatus.

20 Claims, 6 Drawing Sheets

(56) References Cited

U.S. PATENT DOCUMENTS

| | | | |
|---|---|---|---|
| 7,326,232 B2 | 2/2008 | Viola et al. | |
| 7,434,717 B2 * | 10/2008 | Shelton et al. | 227/176.1 |
| 7,455,676 B2 * | 11/2008 | Holsten et al. | 606/139 |
| 7,588,174 B2 * | 9/2009 | Holsten et al. | 227/176.1 |
| 2005/0263562 A1 * | 12/2005 | Shelton et al. | 227/176.1 |
| 2006/0049230 A1 * | 3/2006 | Shelton et al. | 227/180.1 |
| 2007/0175950 A1 * | 8/2007 | Shelton et al. | 227/176.1 |
| 2008/0169333 A1 * | 7/2008 | Shelton et al. | 227/180.1 |
| 2009/0177201 A1 * | 7/2009 | Soltz et al. | 606/75 |
| 2010/0072256 A1 * | 3/2010 | Baxter et al. | 227/180.1 |
| 2011/0315739 A1 * | 12/2011 | Sniffin et al. | 227/176.1 |

\* cited by examiner

This application claims the benefit of U.S. Provisional Patent Application No. 61/253,650 filed Oct. 21, 2009, the disclosure of which is hereby incorporated by reference.

APPARATUS AND METHOD FOR PRESERVING A TISSUE MARGIN

REFERENCE TO RELATED APPLICATIONS

This application claims the benefit of U.S. Provisional Patent Application No. 61/253,650 filed Oct. 21, 2009, the disclosure of which is hereby incorporated by reference.

STATEMENT REGARDING FEDERALLY SPONSORED RESEARCH OR DEVELOPMENT

Not applicable.

BACKGROUND OF THE INVENTION

This invention is a device and the methodology of its use for removing a section of tissue from a patient. More specifically, the device and method cut and secure tissue while preserving a tissue margin for pathological examination.

In both traditional and minimally invasive operations, a section of abnormal tissue, such as cancerous or diseased tissue, as well as cystic adenomatoid malformations, vascular lesions, sequestrations, infected tissue, cavitary lesions, and the like, is removed from a region of otherwise healthy tissue. Many surgeons use a surgical apparatus that both resects the abnormal tissue from the healthy tissue and seals the edges of both surfaces of cut tissue. Sealing the edges of the healthy tissue promotes healing and permits it to function normally. Sealing the edge of the abnormal tissue prevents contamination of the wound during operation and helps maintain the integrity of the specimen to facilitate subsequent dissection.

Many surgeons position the line of resection a short distance from the abnormal tissue to ensure the abnormal tissue is completely removed from the patient. After the operation, a surgical pathologist examines the resection specimen grossly and histologically to determine the nature of the abnormality, its extent, and the distance between the resection line and the closest component of the abnormal tissue. The distance between the resection line and the abnormal tissue provides information for the medical staff to determine if subsequent treatment, such as additional surgery or radiation, is necessary. For example, if the abnormal tissue abuts the resection line, surgery to remove additional tissue may be required. Conversely, if the line of resection is free of abnormal tissue and is a sufficient distance (for example, several millimeters) from it, then no additional treatment may be dictated.

Prior surgical devices deploy rows of fasteners on tissue along a line of division created by the cut of a knife deployed from the same device. This action divides the organ into a specimen side with abnormal tissue and a patient side of tissue that is assumed to be healthy. These rows of fasteners occupy and damage the tissue along the resection line, rendering the margin between healthy and abnormal tissue unavailable to analysis—the tissue with the embedded fasteners (the actual resection margin) is removed and discarded, and the adjacent tissue is then designated the true margin and is removed and examined histologically. This underestimates the distance of the abnormal tissue from the surgical margin. In some situations, the abnormal tissue is very close to the fastened tissue margin because of anatomical constraints or functioning organ tissue cannot be sacrificed as in an infant. Accordingly, a resection margin may be incorrectly identified as being extremely close or positive for abnormal tissue. Unfortunately, any additional surgery or radiation involves loss of more functioning organ tissue and may be accompanied by a serious reduction of organ function, higher risk of postoperative complications and sometimes emotional distress, especially if the patient is elderly or an infant.

Therefore, it is essential to have a surgical apparatus that preserves tissue along the resection line of a tissue specimen, at the true resection margin, that is appropriate for histological examination. It is also important to have a surgical apparatus that reduces the possibility of requiring unnecessary and potentially harmful surgery to remove additional tissue from a patient.

BRIEF SUMMARY OF THE INVENTION

The present invention overcomes the aforementioned drawbacks by providing a surgical apparatus that preserves tissue along the resection line. The present invention provides a tissue margin that is appropriate for histological examination. Hence, the present invention reduces the possibility of requiring unnecessary surgery to remove additional tissue from a patient, and thereby reduces the associated physical risks and further emotional trauma to those involved and undergoing the surgery.

In accordance with one aspect of the invention, a cartridge for a surgical apparatus is disclosed. The cartridge includes a housing having a slot configured to accommodate a blade. A plurality of fasteners is configured to be deployed by the housing. A first row of the plurality of fasteners is positioned on a first side of the slot and a second row of the plurality of fasteners is positioned on a second side of the slot. The first row of the plurality of fasteners is the nearest row of fasteners to the slot on the first side of the slot that are deployed by the housing, and the first row of the plurality of fasteners is spaced apart from the slot such that an undamaged tissue margin is formed on a section of tissue during operation of the surgical apparatus.

In accordance with another aspect of the invention, a method for resecting tissue is disclosed. The method includes the step of cutting the tissue at a cutting location to form a first tissue section and a second tissue section. The method also includes the step of fastening the first tissue section at a first fastening location adjacent to the cutting location. The method further includes fastening the second tissue section at a second fastening location adjacent to the cutting location, and the second fastening location is spaced apart from the cutting location such that an undamaged tissue margin is formed.

Various other features of the present invention will be made apparent from the following detailed description and the drawings.

BRIEF DESCRIPTION OF THE SEVERAL VIEWS OF THE DRAWINGS

The invention will hereafter be described with reference to the accompanying drawings, wherein like reference numerals denote like elements, and.

DETAILED DESCRIPTION OF THE INVENTION

In general, the present invention provides a surgical fastening apparatus that preserves a cuff of true tissue margin at a cutting line between resected tissue and healthy tissue. In some configurations, the specimen side (i.e., resected tissue side) of the fastening apparatus is designed differently from the patient side (i.e., healthy tissue side) to provide the tissue cuff. In some configurations, the fastening apparatus also provides temporary hemostasis during a surgical operation.

Figure 1:
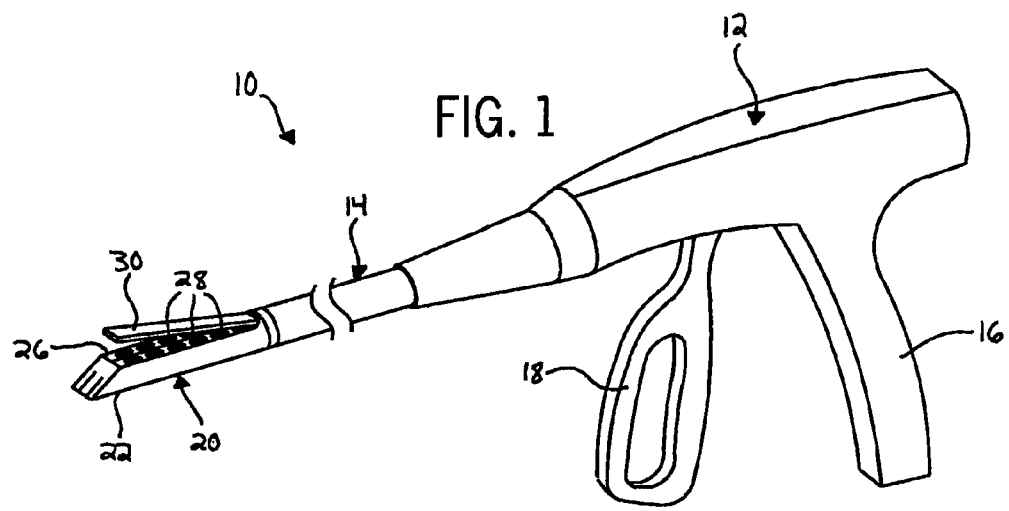
FIG. 1 is a perspective view of a surgical apparatus incorporating the present invention.

Referring now to the figures, the present invention is incorporated in a surgical apparatus 10 that separates multiple tissue sections from one another during a surgical operation. The surgical apparatus 10 also applies a plurality of fasteners to the tissue sections and advantageously provides a tissue margin that is appropriate for histological examination. Referring specifically to FIG. 1, the surgical apparatus 10 includes a handle assembly 12 connected to an elongated assembly 14. The handle assembly 12 includes a stationary handle 16 positioned proximate an actuation handle 18. The actuation handle 18 is moved relative to the stationary handle 16 to use the surgical apparatus 10. The handle assembly 12 may include an extension spring (not shown) to bias the actuation handle 18 away from the use position.

Still referring to FIG. 1, the elongated assembly 14 may be pivotally connected to the handle assembly 12 to permit reorientation of the elongated assembly 14 by a surgeon. The elongated assembly 14 extends generally away from the handle assembly 12 and includes a fastener assembly 20 at an end opposite the end that connects to the handle assembly 12. The elongated assembly 14 also houses components to operatively connect the actuation handle 18 and the fastener assembly 20, such as a control cord, a shaft, or the rack of a rack and pinion assembly (not shown). Those skilled in the art will also recognize other similar components that may be used to operatively connect the actuation handle 18 and the fastener assembly 20.

Figure 2:
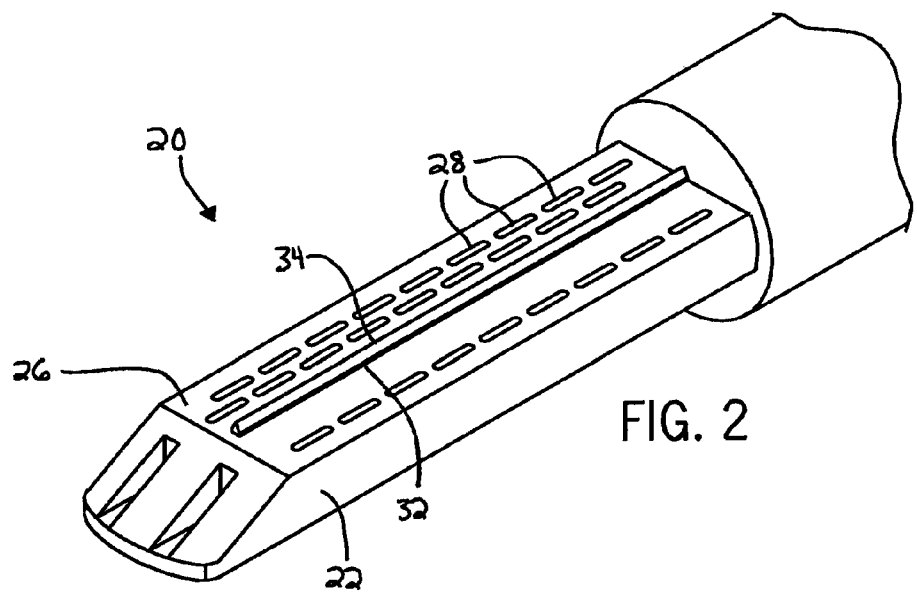
FIG. 2 is a perspective view of a cartridge of the surgical apparatus of FIG. 1.
Figure 3:
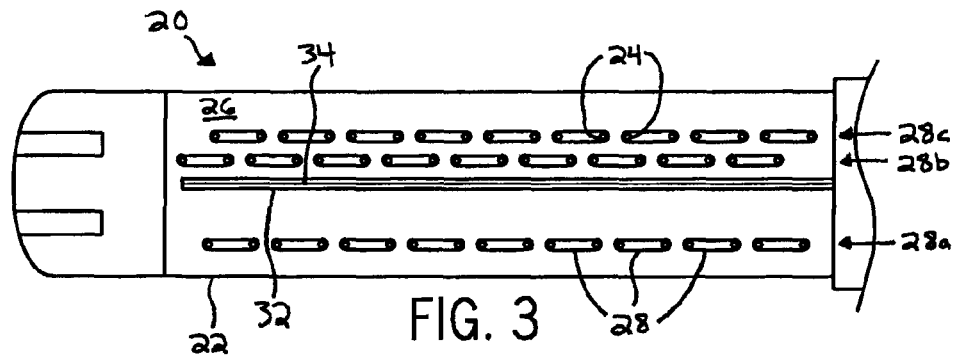
FIG. 3 is a top view of the cartridge of FIG. 2 illustrating rows of fastener openings.

The fastener assembly 20 may be a single-use component that is removably connected to the elongated assembly 14. That is, the fastener assembly 20 may be a cartridge that connects to the elongated assembly 14 and is removed after use. Referring to FIGS. 1-3, the fastener assembly 20 includes a housing 22 that contains a plurality of fasteners 24 (most easily seen as 324 in FIG. 7) before use of the surgical apparatus 10. The housing 22 includes an ejection surface 26 having a plurality of fastener slots, three of which are indicated by reference numeral 28, through which the fasteners 24 pass during use of the surgical apparatus 10. The length of the rows of the fastener slots 28 may be, for example, from 12 to 50 mm.

The fasteners 24 pass through the fastener slots 28 due to fastener ejectors (321 in FIGS. 7 & 8) that move through internal passageways (323 in FIGS. 7 & 8) in response to motion of the actuation handle 18. The fastener ejectors 321 include side walls 325 that push the fasteners 24 through the fastener slots 28 during use of the surgical apparatus 10.

The fastener assembly 20 also includes an anvil member 30 (FIG. 1) positioned proximate the ejection surface 26. During use of the surgical apparatus 10, tissue is positioned between the anvil member 30 and the ejection surface 26. The fasteners 24 are ejected from the fastener slots 28 and pierce the tissue. The anvil member 30 engages and may deform the fasteners 24 to secure the fasteners 24 to the tissue.

Figure 9:
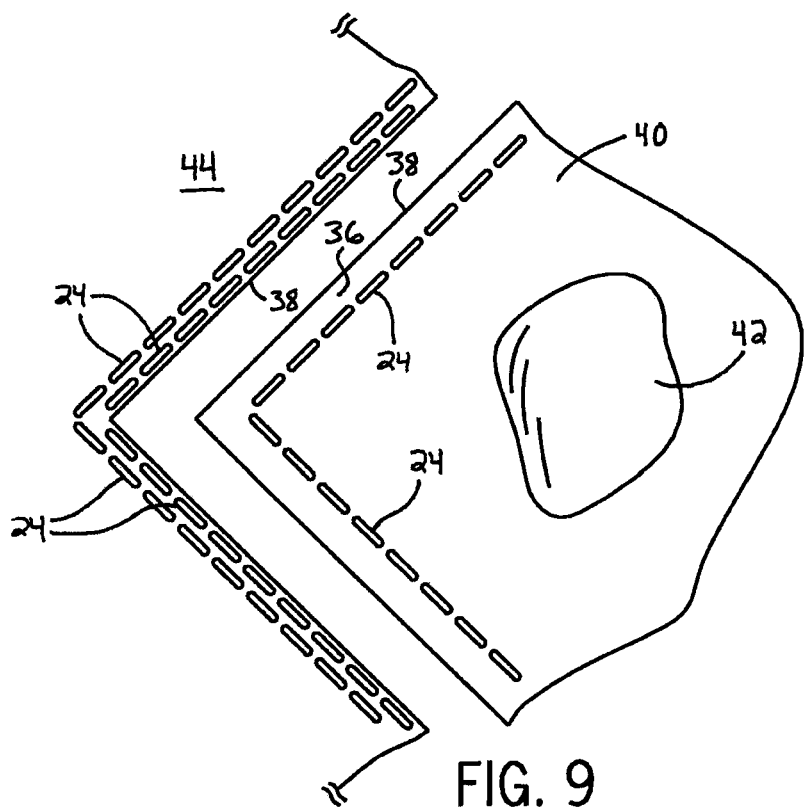
FIG. 9 is a top view of healthy tissue and resected tissue including rows of fasteners after use of the cartridge of FIG. 2.
Figure 10:
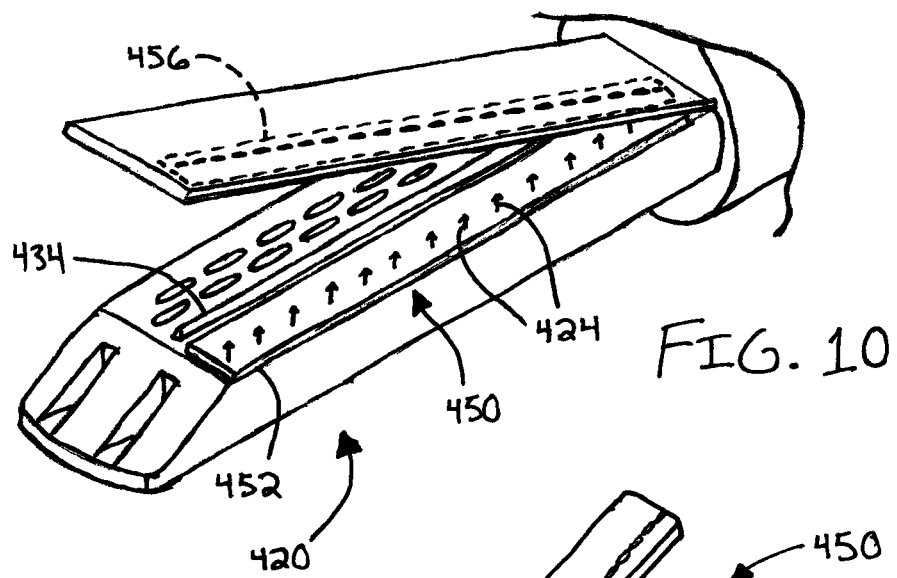
FIG. 10 is a perspective view of yet another alternative configuration of a surgical cartridge according to the present invention.
Figure 11:
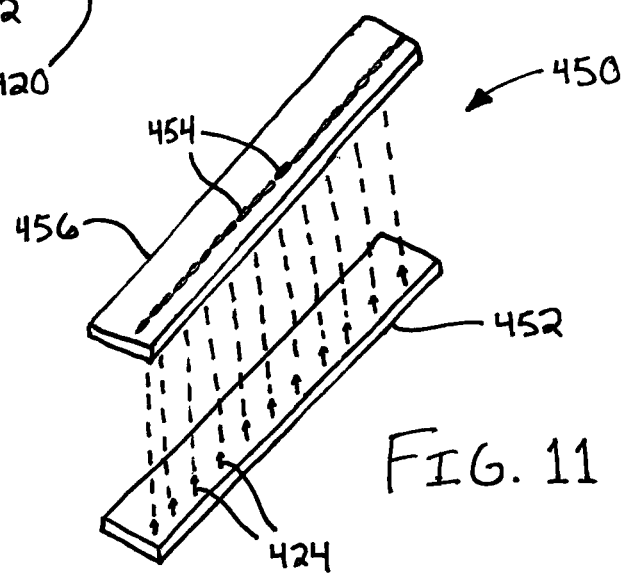
FIG. 11 is a perspective view of compressive members of the cartridge of FIG. 10 separated from each other.
Figure 12:
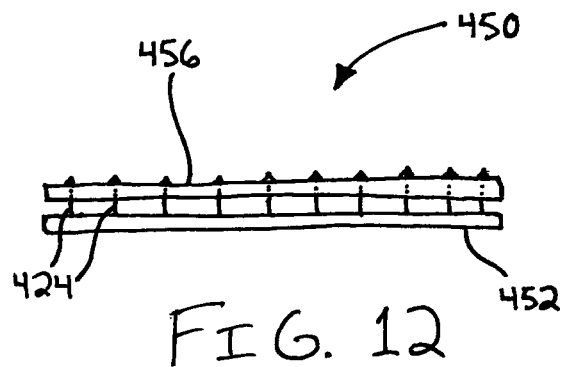
FIG. 12 is a side view of the compressive members of FIG. 11 connected to each other.
Figure 13:
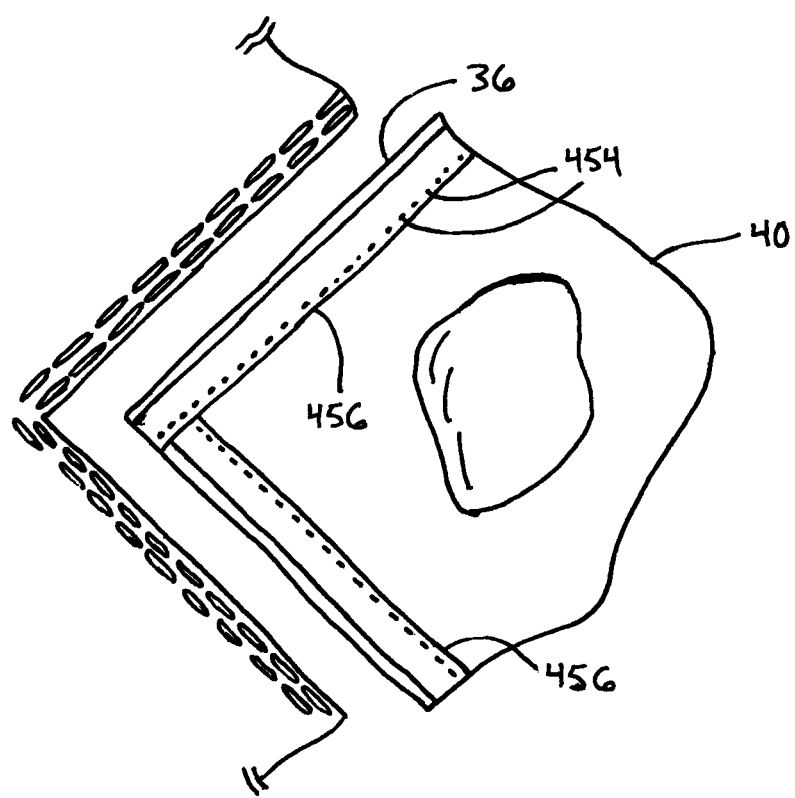
FIG. 13 is a top view of resected tissue supporting the compressive members after use of the cartridge of FIG. 10.

The ejection surface 26 also includes a blade slot 32 that accommodates a blade 34 to separate the tissue into two sections during use of the surgical apparatus 10. The blade 34 may be a relatively short component that translates along the blade slot 32 due to motion of the fastener ejectors 321. The blade 34 is advantageously positioned between rows of the fastener slots 28. Referring to FIG. 3, for example, fastener slot row 28a is positioned on a first side of the blade 34 and fastener slot rows 28b and 28c are positioned on a second side of the blade 34. In addition, the fastener slot row 28a is advantageously spaced apart from the blade 34 by a small distance, for example, from 2 to 4 mm. However, the range of distances may be modified based on tissue characteristics such as elasticity. Referring to FIGS. 3 & 9, the space between the fastener slot row 28a and the blade 34 results in a section of tissue near the resection line 38, or a tissue margin 36 (FIG. 9), that is not damaged by the fasteners 24. The undamaged tissue margin 36 has a width, for example, from 2 to 4 mm and is appropriate for histological examination by a pathologist. Unlike the tissue near the resection line provided by prior art designs, the tissue margin 36 provided by the present invention does not complicate histological examination due to the presence of fasteners and deformation of the tissue caused by the fasteners.

Referring to FIG. 9, the surgical apparatus 10 is used in a manner such that the tissue margin 36 is formed on the resected tissue 40 to permit examination by the pathologist after the resected tissue 40 is removed from the patient. As discussed above, the pathologist determines the distance between the resection line 38 and the actual abnormal tissue 42, such as a tumor, as a reference to determine the need for additional patient treatment. In addition, the tissue margin 36 may be excised from the resected tissue 40 for further histologic examination to determine the presence of abnormal tissue.

Multiple single-use fastener assemblies 20 may be used to remove the abnormal tissue 42 from the healthy tissue 44. For example, as shown in FIG. 9, two fastener assemblies 20 are used to provide two sets of rows of fasteners 24 and remove the abnormal tissue 42 from the healthy tissue 44.

It is contemplated that the present invention may be used with soft tissue, such as lung, stomach, intestine, esophagus tissue, and the like. As a result, the fasteners 24 may be steel surgical staples. However, other types of fasteners 24 may be used, such as two-part surgical fasteners that are well-known to those skilled in the art.

Figure 4:
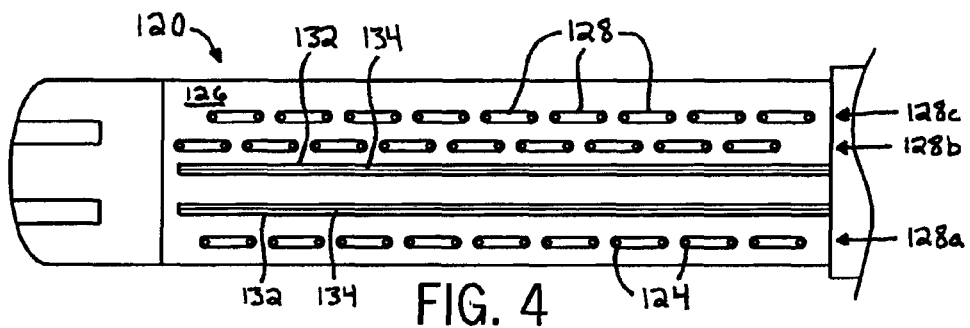
FIG. 4 is a top view of an alternative configuration of the cartridge of FIG. 2.

Referring now to FIG. 4, an alternative configuration of a fastener assembly 120 of the surgical apparatus 10 includes an ejection surface 126 having a plurality of fastener slots, three of which are indicated by reference numeral 128, and two blade slots 132 that each accommodate a blade 134. The blades 134 are advantageously positioned between rows of the fastener slots 128. That is, fastener slot row 128a is positioned on a first side of the blades 134 and fastener slot rows 128b and 128c are positioned on a second side of the blades 134. In addition, the blades 134 are advantageously spaced apart from each other by a small distance, for example, from 2 to 4 mm. The space between the blades 134 results in three separate sections of tissue after use of the surgical apparatus 10. The two sections of tissue to the sides of the blades 134 are secured by fasteners 124 after use of the surgical apparatus 10. The section of tissue between the blades 134 does not include fasteners 124 and is an appropriate tissue margin 36 for subsequent histological examination.

The fastener assembly 120 may be used with a capture and tracking device that encases the tissue margin 36 and provides orientation information of the tissue margin 36. That is, the device indicates the edge of the tissue margin 36 that was proximate the abnormal tissue 42 prior to the operation.

Figure 5:
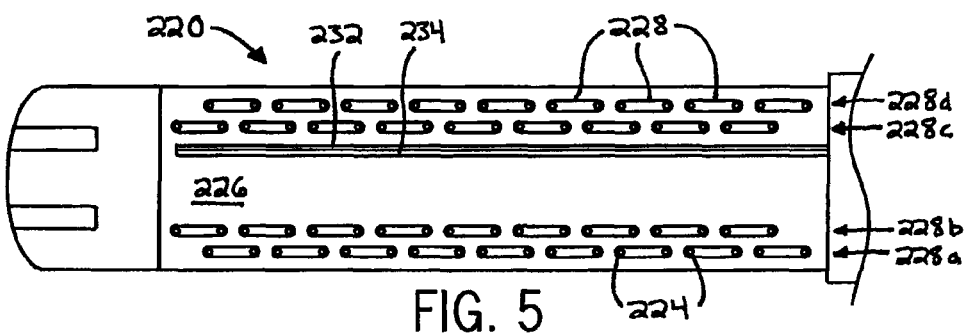
FIG. 5 is a top view of another alternative configuration of the cartridge of FIG. 2.

Referring now to FIG. 5, another alternative configuration of a fastener assembly 220 of the surgical apparatus 10 includes an ejection surface 226 having a plurality of fastener slots, three of which are indicated by reference numeral 228, and a blade slot 232 that accommodates a blade 234. The blade 234 is advantageously positioned between rows of the fastener slots 228. For example, fastener slot rows 228a and 228b are positioned on a first side of the blade 234 and fastener slot rows 228c and 228d are positioned on a second side of the blade 234. In addition, the fastener slot rows 228b and 228c are advantageously spaced apart from the blade 234 by a small distance, for example, from 2 to 4 mm. Like the first configuration of the fastener assembly 20, the space between the fastener slot row 228b and the blade 234 results in a tissue margin 36 that is not damaged by the fasteners 224. The tissue margin 36 may be removed from the resected tissue by a scalpel and is appropriate for histological examination. In addition, the fastener assembly 220 shown in FIG. 5 advantageously provides relatively secure resected tissue 40 due to the presence of two rows of fasteners.

Figure 6:
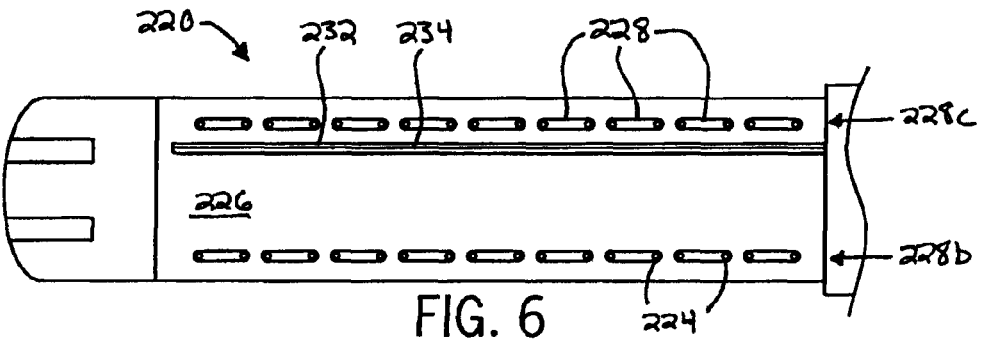
FIG. 6 is a top view of the configuration of the cartridge of FIG. 5 having fewer rows of fastener openings.

The fastener assembly 220 may include a different number of rows of fastener slots 228. Referring to FIG. 6, for example, the fastener assembly 220 may include two rows of fastener slots 228b and 228c positioned on opposite sides of the blade 234.

Figure 7:
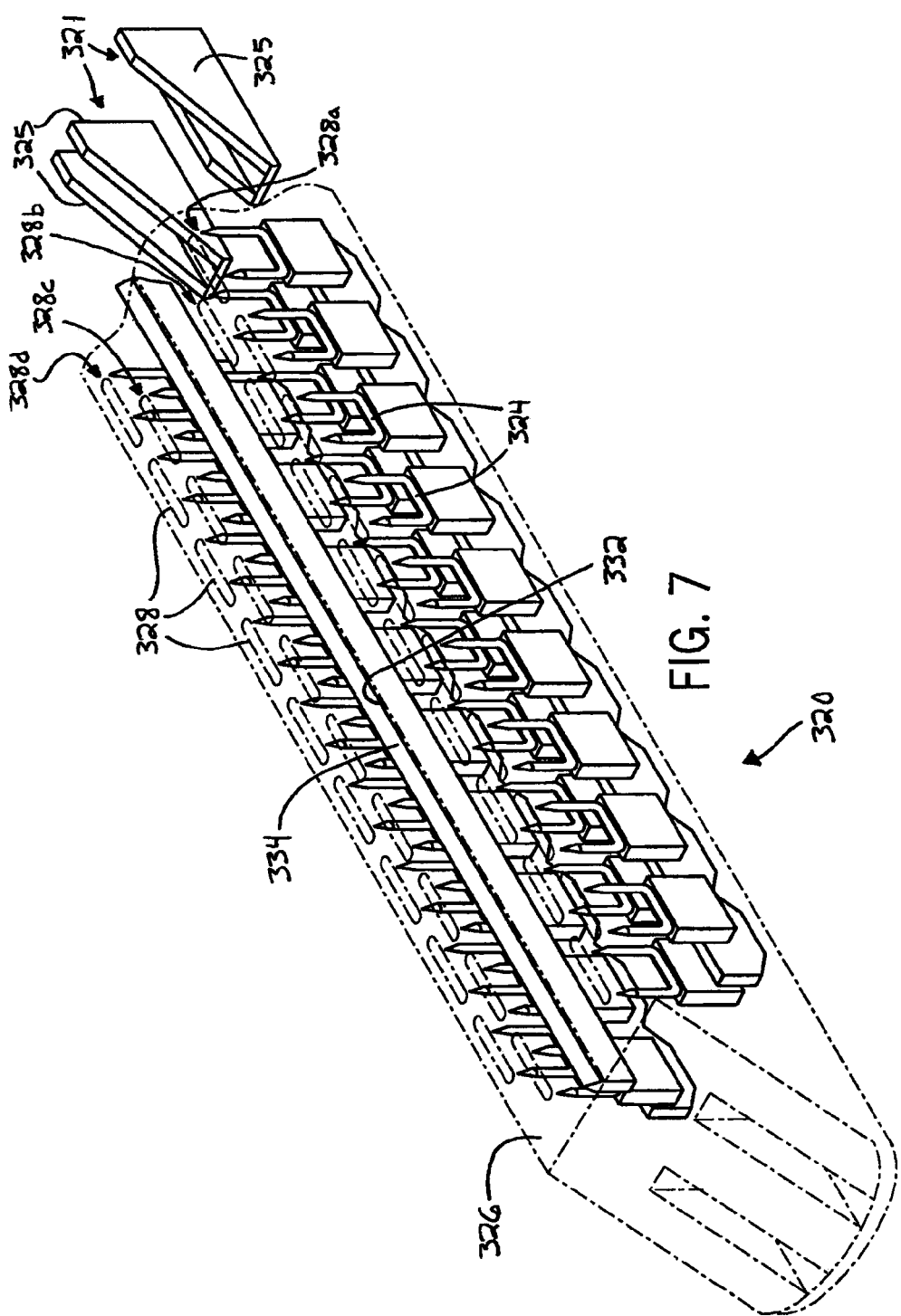
FIG. 7 is a perspective hidden view of yet another alternative configuration of the cartridge of FIG. 2.
Figure 8:
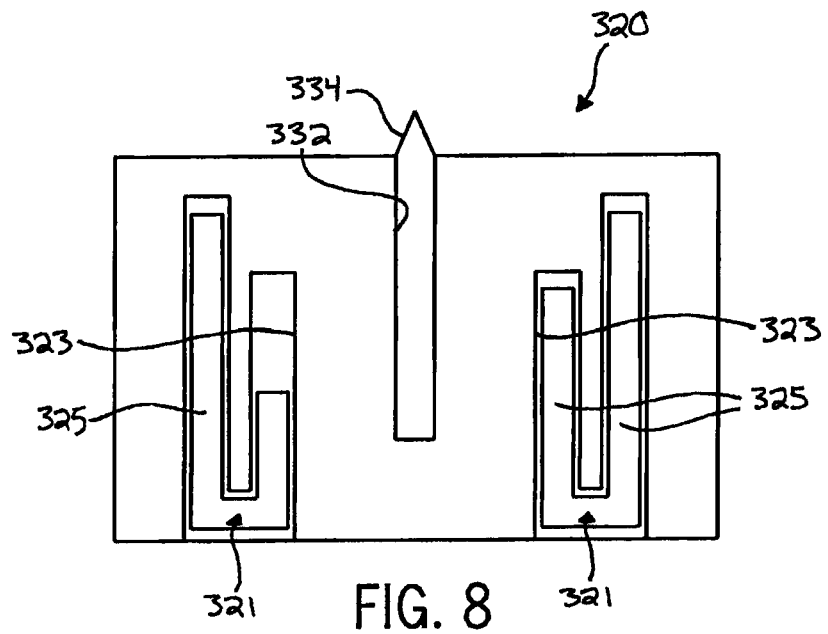
FIG. 8 is a rear view of the configuration of the cartridge of FIG. 7 illustrating fastener ejectors.

Referring to FIGS. 7 and 8, yet another alternative configuration of a fastener assembly 320 of the surgical apparatus 10 includes an ejection surface 326 having a plurality of fastener slots, three of which are indicated by reference numeral 328, and a blade slot 332 that accommodates a blade 334. The blade 334 is advantageously positioned between rows of the fastener slots 328. For example, fastener slot rows 328a and 328b are positioned on a first side of the blade 334 and fastener slot rows 328c and 328d are positioned on a second side of the blade 334. In addition, one of the fastener ejectors 321 is modified such that fasteners 324 are not ejected from one of the rows of the fastener slots 328, for example, fastener slot row 328b or 328c. Modification of the fastener ejector 321 may include removing one of the side walls 325 such that the fastener ejector 321 does not push the fasteners 324 through the fastener slots 328. As a result, the surgical apparatus 10 provides a tissue margin 36 that is not damaged by the fasteners 324. Like in the other configurations of the present invention, the tissue margin 36 may be removed from the resected tissue 40 by a scalpel and is appropriate for histological examination.

Referring now to FIGS. 10-13, yet another alternative configuration of a fastener assembly 420 of the surgical apparatus includes a compressive fastening device 450 instead of a row of separate fasteners that provides an undamaged tissue margin 36. The compressive fastening device 450 includes a first compressive member 452 that supports a plurality of fasteners 424 (e.g., flexible hooks, barbs, or the like). The fasteners 424 are capable of piercing the resected tissue 40 during use and extending through perforations 454 of a second compressive member 456. This action fixes the compressive members 452, 456 to each other with the resected tissue 40 supported there between.

Both compressive members 452, 456 are generally elongated planar components that comprise, e.g., polymers, metals, or the like. As such, the compressive members 452, 456 are relatively stiff components and are thereby capable of providing temporary hemostasis during excision by compressing tissue there between. In addition, the fasteners 424 and perforations 454 are spaced apart from the blade 434 to provide an undamaged tissue margin 36 for frozen section analysis. Following retrieval of the resected tissue 40, the compressive members 452, 456 are either separated from the tissue (e.g., by deforming the fasteners 424) or processed for histologic diagnosis.

Yet another alternative configuration, the fastener assembly could be wider than current fastener designs. In this case, two rows of fasteners could be positioned on each side of a central blade, and the nearest row of fasteners to the blade on each side could be offset from the blade by the same distance (e.g., 2 to 4 mm).

Those skilled in the art will recognize that the present invention can also be applied to other surgical devices similar to those described above. For example, the present invention can be modified for use with a surgical device having arcuate rows of fastener slots and providing an arcuate resection line. As another example, the surgical device may include a flexible elongated assembly for repositioning of the fastener assembly. As yet another example, the surgical device may include an alternative handle assembly design. Many types of handle assemblies are known in the art, and some do not connect to elongated assemblies.

The present invention has been described in terms of the various embodiments, and it should be appreciated that many equivalents, alternatives, variations, and modifications, aside from those expressly stated, are possible and within the scope of the invention. Therefore, the invention should not be limited to a particular described embodiment.

We claim:

1. A cartridge for a surgical apparatus, comprising:
   a housing including a slot configured to accommodate a blade;
   a plurality of fasteners configured to be deployed by the housing, a first row of the plurality of fasteners being positioned on a first side of the slot, a second row of the plurality of fasteners being positioned on a second side of the slot;
   wherein the first row of the plurality of fasteners is the nearest row of fasteners to the slot on the first side of the slot that are deployed by the housing, and the first row of the plurality of fasteners is spaced apart from the slot such that an undamaged tissue margin is formed on a section of tissue during operation of the surgical apparatus; and
   wherein the housing includes a third row of the plurality of fasteners positioned on the first side of the slot between the first row of the plurality of fasteners and the slot, and wherein the third row of the plurality of fasteners are not deployed by the housing during operation of the surgical apparatus.

2. The cartridge of claim 1, wherein a distance between the first row of the plurality of fasteners and the slot is at least 2 mm.

3. The cartridge of claim 1, wherein the third row of the plurality of fasteners is positioned on the second side of the slot.

4. The cartridge of claim 3, wherein a distance between the third row of the plurality of fasteners and the slot is generally identical to a distance between the first row of the plurality of fasteners and the slot.

5. The cartridge of claim 1, wherein the second row of the plurality of fasteners is the nearest row of fasteners to the slot on the second side of the slot through which fasteners are configured to pass, and a distance between the second row of the plurality of fasteners and the slot is at most 1 mm.

6. The cartridge of claim 1, wherein the slot is a first slot and the blade is a first blade, the housing further includes a second slot configured to accommodate a second blade, and wherein the second slot is positioned between the first slot and the first row of the plurality of fasteners.

7. The cartridge of claim 6, wherein a distance between the first slot and the second slot is at least 2 mm.

8. The cartridge of claim 6, wherein the third row of the plurality of fasteners is positioned on the second side of the first slot.

9. The cartridge of claim 1, wherein the slot, the first row of the plurality of fasteners, and the second row of the plurality of fasteners are generally linear.

10. The cartridge of claim 1, wherein the housing further includes a plurality of fastener openings, and each of the plurality of fasteners is configured to pass through one of the plurality of fastener openings.

11. The cartridge of claim 1, wherein the first row of the plurality of fasteners is supported by a first compressive member that is detachable from the housing.

12. The cartridge of claim 11, wherein the first row of the plurality of fasteners is configured to engage a second compressive member to thereby secure the first compressive member to the second compressive member.

13. A cartridge for a surgical apparatus, comprising:
a housing having a surface including:
a slot configured to accommodate a blade;
an upper surface including a plurality of fastener openings, a first row of the plurality of fastener openings being positioned adjacent to the slot on a first side of the slot, and a second row of the plurality of fastener openings being positioned adjacent to the slot on a second side of the slot;
a plurality of fasteners, each of the fasteners being configured to pass through one of the fastener openings;
wherein a distance between the first row of the plurality of fastener openings and the slot is at least 2 mm; and
wherein the slot is a first slot and the blade is a first blade, the housing further includes a second slot configured to accommodate a second blade, and wherein the second slot is positioned between the first slot and the first row of the plurality of fastener openings.

14. The cartridge of claim 13, wherein a distance between the second row of the plurality of fastener openings and the first slot is at most 1 mm.

15. A cartridge for a surgical apparatus, comprising:
a housing including a first slot configured to accommodate a first blade and a second slot configured to accommodate a second blade;
a plurality of fasteners configured to be deployed by the housing, a first row of the plurality of fasteners being positioned on a first side of the first slot, a second row of the plurality of fasteners being positioned on a second side of the first slot, and the second slot positioned between the first slot and the first row of the plurality of fasteners;
wherein the first row of the plurality of fasteners is the nearest row of fasteners to the first slot on the first side of the first slot that are deployed by the housing, and the first row of the plurality of fasteners is spaced apart from the first slot such that an undamaged tissue margin is formed on a section of tissue during operation of the surgical apparatus.

16. The cartridge of claim 15, further comprising a third row of the plurality of fasteners positioned on the second side of the first slot.

17. The cartridge of claim 16, wherein a distance between the third row of the plurality of fasteners and the first slot is generally identical to a distance between the first row of the plurality of fasteners and the first slot.

18. The cartridge of claim 15, wherein the second row of the plurality of fasteners is the nearest row of fasteners to the first slot on the second side of the slot through which fasteners are configured to pass, and a distance between the second row of the plurality of fasteners and the first slot is at most 1 mm.

19. The cartridge of claim 15, wherein the first row of the plurality of fasteners is supported by a first compressive member that is detachable from the housing.

20. The cartridge of claim 19, wherein the first row of the plurality of fasteners is configured to engage a second compressive member to thereby secure the first compressive member to the second compressive member.

* * * * *

UNITED STATES PATENT AND TRADEMARK OFFICE
CERTIFICATE OF CORRECTION

| | | |
|---|---|---|
| PATENT NO. | : 8,523,042 B2 | Page 1 of 1 |
| APPLICATION NO. | : 12/909298 | |
| DATED | : September 3, 2013 | |
| INVENTOR(S) | : Masiakos | |

It is certified that error appears in the above-identified patent and that said Letters Patent is hereby corrected as shown below:

In the Specifications

Column 1, Line 10-13

Please insert the following after the CROSS-REFERENCE TO RELATED APPLICATIONS paragraph and before the BACKGROUND OF THE INVENTION title:

--STATEMENT REGARDING FEDERALLY SPONSORED RESEARCH
This invention was made with Government support under Grant No. W81XWH-072-0011 awarded by the U.S. Department of the Army. The Government has certain rights in this invention.--

Signed and Sealed this
Sixth Day of May, 2014

Michelle K. Lee
*Deputy Director of the United States Patent and Trademark Office*